(12) United States Patent
Boyd et al.

(10) Patent No.: US 9,566,390 B2
(45) Date of Patent: Feb. 14, 2017

(54) MEDICATION DELIVERY DEVICE

(75) Inventors: Malcolm Stanley Boyd, Warwickshire (GB); Robert Veasey, Warwickshire (GB); David Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1294 days.

(21) Appl. No.: 13/139,693

(22) PCT Filed: Dec. 21, 2009

(86) PCT No.: PCT/EP2009/067609
§ 371 (c)(1),
(2), (4) Date: Oct. 22, 2011

(87) PCT Pub. No.: WO2010/072698
PCT Pub. Date: Jul. 1, 2010

(65) Prior Publication Data
US 2012/0123347 A1     May 17, 2012

(30) Foreign Application Priority Data

Dec. 23, 2008   (EP) ..................................... 08022329

(51) Int. Cl.
| | | |
|---|---|---|
| *A61M 5/32* | (2006.01) | |
| *A61M 5/50* | (2006.01) | |
| *A61M 5/24* | (2006.01) | |
| *A61M 5/315* | (2006.01) | |

(52) U.S. Cl.
CPC ............. *A61M 5/3202* (2013.01); *A61M 5/24* (2013.01); *A61M 5/31511* (2013.01); *A61M 5/31541* (2013.01); *A61M 5/50* (2013.01); *A61M 5/3158* (2013.01); *A61M 5/31525* (2013.01); *A61M 5/3213* (2013.01); *A61M 2205/27* (2013.01)

(58) Field of Classification Search
CPC .... A61M 5/3202; A61M 5/3213; A61M 5/50; A61M 5/24; A61M 5/31511; A61M 5/31541; A61M 5/31525; A61M 5/3158; A61M 2205/27; Y10S 128/919
See application file for complete search history.

(56) References Cited

U.S. PATENT DOCUMENTS

| | | | |
|---|---|---|---|
| 5,259,840 A | | 11/1993 | Boris |
| 5,403,288 A | * | 4/1995 | Stanners ...................... 604/232 |
| 5,484,413 A | | 1/1996 | Gevorgian |

(Continued)

FOREIGN PATENT DOCUMENTS

WO     2007011888 A2    1/2007

OTHER PUBLICATIONS

Form PCT/IB/326, Notification Concerning Transmittal of International Preliminary Report on Patentability.
(Continued)

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

A medication delivery device comprises a housing (1), a cap (2) configured to be attached to the housing (1) and a locking means (16, 17) configured to lock the cap (2). In a first state the cap (2) is detachable and in a second state the locking means (16, 17) locks the cap (2) if the cap (2) is attached.

15 Claims, 2 Drawing Sheets

(56) References Cited

U.S. PATENT DOCUMENTS

| | | | | |
|---|---|---|---|---|
| 5,997,513 A | * | 12/1999 | Smith | A61M 5/3202 128/919 |
| 2004/0127857 A1 | * | 7/2004 | Shemesh | A61M 5/326 604/198 |
| 2008/0108953 A1 | | 5/2008 | Moser et al. | |

OTHER PUBLICATIONS

Communication Pursuant to Article 94(3) EPC issued in European Patent Application No. 09804025.6 dated Mar. 4, 2016.

* cited by examiner

MEDICATION DELIVERY DEVICE

CROSS REFERENCE TO RELATED APPLICATIONS

The present application is a 35 U.S.C. 371 National Application of PCT/EP2009/067609 filed Dec. 21, 2009 and claims priority to European Patent Application No. 08022329.0, filed Dec. 23, 2008, the entire contents of which are incorporated entirely herein by reference.

The invention concerns a medication delivery device comprising a cap.

A medication delivery device may have a cap which is attachable to a distal part of a housing of the medication delivery device. Delivery means located at the distal part of the housing or a drug contained by the distal part of the housing may be protected by the cap. The cap is detached before medication delivery and attached after medication delivery.

A medication delivery device may have lock-out features as part of a delivery mechanism, which prevents the user from trying to set or dial a dose when a predefined quantity of medication has been dispensed.

US 2008/0108953 A1 shows a pen-type medication delivery device for injecting a substance from an ampoule inserted in the device. A delivery mechanism of the device comprises a rod. A safety lock is provided which stops the movement of the rod when the last dose has been dispensed. Thus, the medication delivery device can no longer be primed, which indicates to the user that the last dose has been delivered.

It is an aim of the present invention to provide an additional or alternative feature indicating to the user that the last dose has been delivered.

For this aim a medication delivery device is provided comprising a housing, a cap configured to be attached to the housing and locking means configured to lock the cap. In a first state the cap is detachable and in a second state the locking means locks the cap if the cap is attached. The cap can no longer be detached. In other words, once the cap has been attached the cap is not detachable during the second state.

Embodiments of medication delivery devices may be used to deliver liquid or gel medications, e.g. insulin, human growth hormone, heparin, in particular low molecular weight heparin, their analogues and their derivatives. One embodiment of the medication delivery device is designed as pen-type delivery device. This type of medication delivery device has an elongated housing and a detachable cap for covering the distal part of the housing containing the drug. The device may be configured to dispense fixed doses of the drug, in particular doses which may not be varied by the user, or variable, preferably user-settable, doses of the drug.

The locking means may comprise a radially protruding portion. The locking means may be a resilient member or a resiliently mounted member. The locking means may be fixed to the housing or formed unitarily with the housing. The locking means may be shaped L-like.

When the user tries to detach the cap during the second state, the locked cap clearly indicates the end of life of a disposable medication delivery device. The cap is locked permanently. The locked cap and the housing encapsulate the drug at the end of life of the medication delivery device. The term "end of life" means that the last dose of drug has been delivered. The term is not limited to a disposable medication delivery device. If the medication delivery device is reusable "end of life" means that when the last dose has been delivered, the medication delivery device can be refilled.

Contrary to the device described here, the cap of a conventional medication delivery device only having lock-out features as part of the delivery mechanism remains detachable so that in some cases remaining drug is clearly visible through a window in the housing. The window is often located in the distal part of the housing which can be covered by the cap. When the last dose of the drug has been delivered, the user may try to extricate the remaining drug if the remaining drug is clearly visible.

A benefit of the invention is that the locked cap covers a window in the distal part of the housing at the end of life of the medication delivery device. This results in preventing the user from trying to set or dial a dose when a predefined quantity of drug has been dispensed. The risk that the user may try to extricate the remaining drug at the end of life is reduced by encapsulating the cartridge with a locked cap that is not detachable.

When the last dose has been delivered, a predetermined amount of the drug remains in the medication delivery device. This unused medication (ullage) is not delivered and remains in the medication delivery device at the end of life of the device.

One embodiment of the medication delivery device is configured to deliver a multitude of doses of the drug. When the last dose has been delivered, the cap is locked if the cap is attached after delivery of the last dose.

If the medication delivery device is designed as a reusable device, the locked cap indicates that the medication delivery device has to be refilled. An embodiment of a reusable medication delivery device containing a drug-filled cartridge is refilled by removing the empty cartridge, inserting a new cartridge containing the drug and resetting the delivery mechanism. The locked cap may be unlocked when the cartridge is removed. Another embodiment of a reusable medication delivery device comprises a disposable unit which can be removed after delivering the last dose. If the cap is locked, the disposable unit including the cap which covers the disposable unit is at least partly removed.

One embodiment of the medication delivery device comprises a moveable element, wherein, if the cap is attached, the locking means locks the cap when the element is positioned in a given position. A preferred given position is the position the element reaches when the last dose is delivered. Mostly preferred, the element is part of a delivery mechanism, e.g. the element is designed as a piston rod. The piston rod is configured to push a bung along a drug containing cartridge. The drug is expelled through a needle located at the distal part of the cartridge when the bung moves along the cartridge.

One embodiment of the element is configured to move in a translational direction. Another embodiment of the element is configured to move rotationally and translate.

Preferred embodiments of the locking means are configured to protrude from the housing when the element reaches the given position. One embodiment of the housing has an aperture designed such that the locking means are pushed through the aperture.

When the cap is attached, the protruding locking means is coupled with mating means of the cap so that the cap is locked. In one embodiment the cap's mating means is formed as a recess for inserting the protruding locking means.

Other features will become apparent from the following detailed description when considered in conjunction with the accompanying drawings.

FIG. 1 shows an embodiment of a pen-type medication delivery device comprising a housing 1 and a cap 2.

Figure 1:
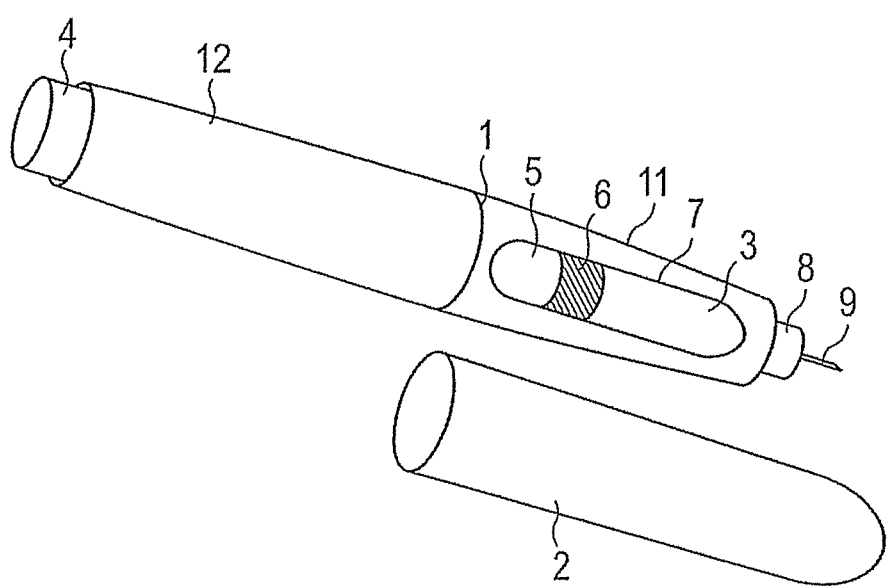
FIG. 1 shows an embodiment of a pen-type medication delivery device.

The housing 1 has a distal part 11 and a proximal part 12. The distal part 11 is configured to contain a drug. In one embodiment the distal part 11 serves as cartridge holder and is configured to contain a cartridge made of e.g. glass, the cartridge containing the drug. The cartridge has a distal end covered by a membrane. A bung 6 moveable to the distal direction is located at the proximal end of the cartridge.

A needle unit 8 comprising a needle 9 for delivering the drug is attached to the distal end 11 of the housing. Before an injection is administered, the needle unit 8 is attached to the housing 1 so that a proximal end of the needle 9 punctures the membrane of the cartridge. The needle unit 8 can be detached after the injection has been administered.

A delivery mechanism of the medication delivery device comprising setting means 4 and a piston rod 5 is located at least partly inside the housing 1. One embodiment of the delivery mechanism is designed such that a fixed dose is set and delivered. An alternative embodiment of the delivery mechanism is designed to adjust the dose to be set and delivered.

The setting means 4 are located partly in the proximal part 12 of the housing. A part of the setting means 4 sticks out of the proximal end of the housing 1. The setting means 4 is configured to set a dose of the drug. When the setting means 4 is moved to a first direction the dose is set. When the setting means 4 is moved to a second direction the dose is delivered. In one embodiment the dose is set when the setting means is pulled to the proximal direction and the dose is delivered when the setting means is pushed to the distal direction. In another embodiment the dose is set when the setting means is rotationally moved and the dose is delivered when the setting means is moved to the distal direction.

A piston rod 5 located inside the housing 1 can be moved from a starting position to an end position. The distal end of the piston rod 5 is coupled to the bung 6 so that it advances along the cartridge in the distal direction when the piston rod 5 moves to the distal direction.

A window 7 or transparent region in the housing 1 shows the position of the bung 6, the position indicating the drug available inside the cartridge.

The setting means 4 and the piston rod 5 are coupled. The piston rod 5 moves to the distal direction pushing the bung 6 along the cartridge when the setting means 4 moves to the second direction. The drug is expelled through the needle 9, when the bung 6 moves along the cartridge.

When the medication delivery device is not in use the cap 2 is normally attached to the housing 1 so that the distal part 11 is covered. The attached cap 2 protects the distal part 11 of the housing containing the drug if the medication delivery device is not used. A snapping means (not shown) prevents that the cap 2 accidentally slides from the housing 1. Before the injection is administered the cap is detached from the housing 1. The cap 2 is removed from the housing 1 and can be put aside during injection. After injection the cap 2 is reattached to protect the cartridge 121.

During a first state or normal operation state, wherein the medication delivery device contains sufficient drug to deliver at least one dose, the cap is detachable.

When the last dose has been delivered, the medication delivery device switches to a second state, wherein the cap 2 is locked when it is attached. In other words, after delivering the last dose, the cap 2 is attached and cannot be removed any longer. The cap 2 is not detachable.

The lock-out of the cap 2 prevents access to the cartridge and gives a clear indication to the user that the device is not meant to be used again. The lock-out of the cap 2 could be used in addition to a delivery mechanism lock-out feature or as a complete device lock-out feature in isolation.

In addition to this, during device disposal of conventional disposable pen-type medication delivery devices, the cap may get lost, and if the cartridge should break, drug could leak out of the device. With the cap 2 locked onto the device prior to disposal, this minimizes the risk of broken glass or drug escaping should the cartridge break.

The lock-out of the cap 2 prevents the user from removing the cap 2 once it has been replaced after the final dose has been delivered. Any remaining drug is encapsulated in a safe enclosure. Advantageously this has two benefits; primarily it prevents the user from trying to access any of the remaining undispensed drug, and secondarily it minimizes the risk of glass fragments escaping should the cartridge break during disposal. The locked cap makes the disposable device safer in the end-of-life condition and reduces the risk of contamination from used needles.

Figure 2:
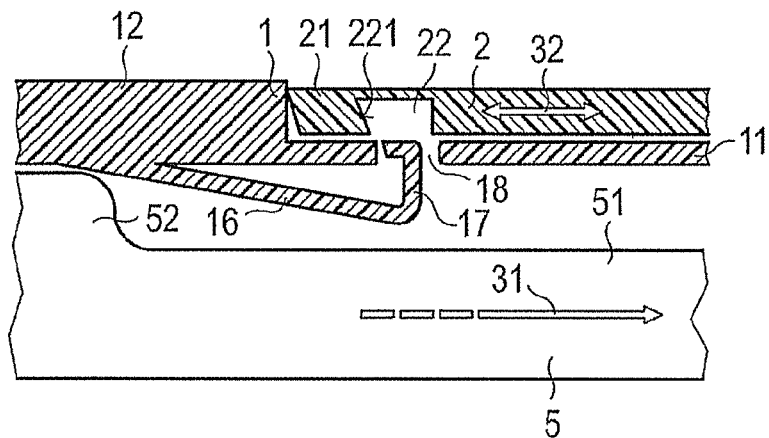
FIG. 2 shows a detailed section of an embodiment of a pen-type medication delivery device during a first state, wherein the cap is detachable.

FIG. 2 shows a detailed section of one embodiment of a pen-type medication delivery device during the first state. The section shows parts of the housing, the attached cap and the piston rod located inside the housing. For clarity reasons a cartridge is not shown.

The cap 2 of the pen-type medication delivery device is attached to the housing 1 so that the distal part 11 of the housing is covered. During the first state, the cap 2 and the housing 1 are detachably connected if the cap 2 is attached to the housing 1, as indicated by a double arrow 32. One embodiment of a detachable connection is a snap fit (not shown). In one embodiment the attached cap is at least partly rotatable. In another embodiment the position of the attached cap is fixed.

The cap 2 comprises a recess 22 located in the inside wall of the cap 2. One embodiment of the recess is formed as circumferential trench or groove in the inner wall of the cap. One embodiment of the recess is formed as a cavity. The recess 22 serves as mating means as will be explained later.

An aperture 18 is located in the distal part 11 of the housing. The position of the aperture 18 may be aligned with the position of the recess 22, if the cap 2 is attached.

A clip 16, 17 serving as locking means is located inside the housing 1. The clip 16, 17 comprises a radially protruding portion. The clip 16, 17 may be secured against displacement with respect to the housing 1. The clip 16, 17 may be a resilient member or it may be resiliently mounted to the housing 1.

The clip 16, 17 comprises a first part 16 and a second part 17. A proximal end of the first part 16 is connected with the housing 1, the first part 16 extending angularly to the inside wall of the housing 1. A second part 17 of the clip 16, 17 connected with the distal end of the first part 16 extends orthogonally or almost orthogonally, to the first part 16.

The clip 16, 17 is configured such that the second part 17 of the clip 16, 17 extends through the aperture 18 when the first part 16 of the clip moves towards the inside wall of the housing 1.

One embodiment of the clip 16, 17 is integrally formed with the housing 1. The first part 16 of the clip 16, 17 is moveable due to the flexibility of the material. Another embodiment of the clip 16, 17 is coupled with the housing via a hinge.

The clip 16, 17 may be shaped L-like. However, the form of the clip 16, 17 is not limited to L-shape or hook-shape. Other embodiments of locking means configured to protrude from the housing are also suitable.

A piston rod 5 comprising a distal part 51 and a proximal part 52 is located inside the housing 1. The piston rod 5 is moveable to the distal direction along the clip 16, 17 and the aperture 18 as indicated by arrow 31. The first part 51 of the piston rod 5 is configured such that it does not push the clip 16, 17 towards the inside wall of the housing 1 when this part moves along the first part 16 of the clip 16, 17. The second part 52 of the piston rod 5 serves as a last-dose-lock activating feature. It is configured such that the first part 16 of the clip 16, 17 is pushed to the inside wall of the housing 1 when this part of the piston rod 5 moves along the first part 16 of the clip 16, 17.

In one embodiment the second part 52 of the piston rod 5 is formed cylindrically having a larger diameter than the cylindrically formed first part 51 of the piston rod 5. Alternatively, the second part 52 of the piston rod 5 comprises an elevation configured to push the first part 16 of the clip 16, 17. In an alternative embodiment the piston rod 5 is formed cylindrically. The first part 51 of the piston rod 5 is designed such that the clip 16, 17 does not contact the piston rod 5 and is not pushed when the first part 51 of the piston rod 5 moves relative to the clip. The term "cylindrical" describes the basic form. Embodiments having a structured cylinder barrel with protrusions, helixes or threads are also included by the term "cylindrical".

During the first state the clip 16, 17 is positioned in an initial position. The second part 17 of the clip 16, 17 does not protrude from the outer wall of the housing 1. The cap 2 is detachable. The first part 51 of the piston rod 5 is positioned adjacent to the clip 16, 17, but does not push the clip 16, 17.

For injecting a dose the cap 2 is removed, then the piston rod 5 pushes the cartridge bung (not shown in FIG. 2) into the distal direction so that the drug is delivered. The cap 2 can be attached after the injection.

When the last dose is being delivered, the piston rod 5 moves to the distal direction so that the second part 52 of the piston rod 5 moves towards the first part 16 of the clip 16, 17 and pushes the first part 16 of the clip 16, 17 towards the inner wall of the housing 1. The movement of the clip 16, 17 results in pushing the second part 17 of the clip 16, 17 through the aperture 18.

The clip 16, 17 serves as locking means, which are not engaged with the cap 2 until the second part 52 of the piston rod 5 reaches its end-of-life position. The end-of-life position is the position of the piston rod 5 after the last dose has been delivered. The term "end-of-life position" is not limited to disposable medication delivery devices, but also describes the position of the piston rod 5 after the last dose has been delivered and before a reusable medication delivery device is refilled and the piston rod 5 is reset.

The second part 52 of the piston rod 5 serves as activating means for engaging the locking means. Once the end-of-life position is reached, the activating means forces the second part 17 of the flexible clip 16, 17 through the aperture 18. In particular, the second part 17 is moved radially, in particular from the inside of the housing 1 to the outside of the housing 1. After the second part 17 of the flexible clip 16, 17 has been pushed through the aperture 18 the second part 52 can lock into the corresponding recess 22 of the cap 2 preventing the cap 2 from being removed once it has been attached.

In another embodiment another axially incrementing component of the medication delivery device serves as pushing means and impacts on the locking means. The lock-out principle can be achieved for both translational drive mechanisms and rotational drive mechanisms.

Figure 3:
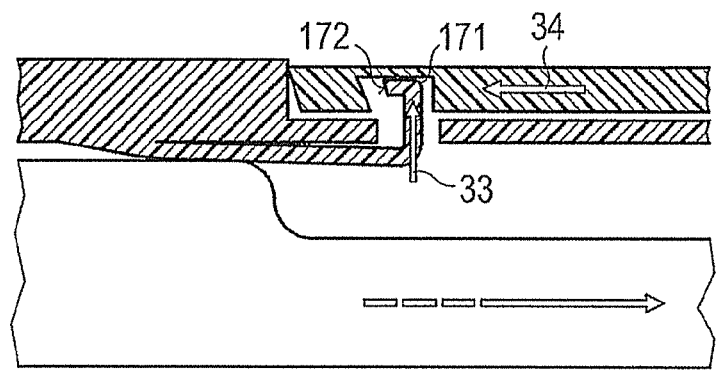
FIG. 3 shows a detailed section of the pen-type medication delivery device during a second state, wherein the cap is not detachable.

FIG. 3 shows the section of the pen-type medication delivery device during the second state.

The second part 52 of the piston rod 5 has reached its end-of-life position and is located such that the first part 16 of the clip 16, 17 is pushed and the second part 17 protrudes from the housing 1 (as indicated by arrow 33).

The protruding second part 17 of the clip 16, 17 is designed such that the cap 2 slides over it during attachment. In this embodiment a distal edge 171 of the protruding part of the clip 16, 17 is formed as rounded edge.

After delivery of the last dose, the cap 2 can be attached as indicated by arrow 34. In particular, the cap 2 can be attached by moving the cap 2 in the axial, in particular proximal, direction with respect to the housing 1 and with respect to the clip 16, 17. Due to the sloped proximal edge 21 of the cap and the rounded edge 171 of the protruding flexible clip, the cap 2 moves over the protruded locking means, bending it down so that the cap 2 slides over the locking means until the recess 22 reaches the locking means. When the recess 22 has reached the locking means, it snaps back to its protruding position and engages with the recess 22.

In a preferred embodiment the locking means and the recess are aligned such that the cap 2 is locked in its attachment position.

The second part 17 of the clip 16, 17 engages with the recess 22 in the cap 2, the recess 22 serving as mating means. The recess 22 comprises an undercut 221. The end of the clip 16, 17 is hook-shaped, configured to engage with the undercut 221 when the user tries to move the cap 2 into the distal direction.

A rotatably attachable cap 2 with a circumferential trench forming the mating means remains rotatable after the cap 2 has been locked, because the locking means engaged with the trench prevents distal movement of the cap 2, but does not prevent rotational movement. If the recess is formed as cavity the rotational movement is prevented when the locking means engages with the recess. In this case the cap 2 may rotate until the recess reaches the locking means.

One embodiment of the medication delivery device comprises more than one locking means, e.g. two or three. One embodiment of the medication delivery device comprises a number of mating means, so that the cap 2 can be locked in different rotational positions.

The cap 2 is permanently locked at the end of life of the pen-type medication delivery device. This feature provides additional feedback to the user that the device has reached end of life. In conjunction with this, the feature allows the device to seal unused medicament once the cap has been replaced at the end of life. A further benefit is that once sealed, the device is safe for disposal, as any cartridge breakage is prevented by the encapsulating cap; consequently, there is less risk of glass fragments escaping and reduced medicament leakage from the device should the cartridge shatter.

The invention is not limited to a disposable medication delivery device. The invention could be integrated with a reuseable device such that the cap 2 would only unlock once a new cartridge has been loaded into the device and the device has been reset, so that the piston rod 5 no longer locks the cap via the locking element. It could even be part of a disposable unit of a reuseable medication delivery device, encapsulating the used cartridge for disposal.

The advantages of a removable disposable unit would include safer disposal, whereas in a completely re-useable device the advantage would be additional indication to the user that the device has finished delivery and requires reloading and resetting.

Figure 4:
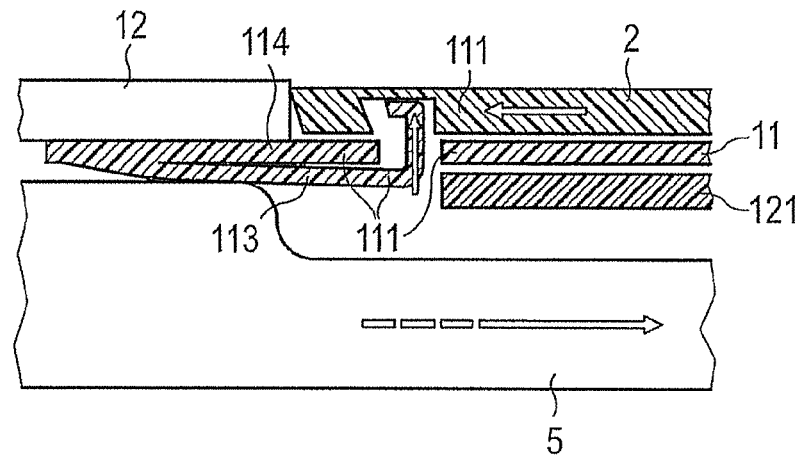
FIG. 4 shows a detailed section of another embodiment of a pen-type medication delivery device during a second state, wherein the cap is not detachable.

FIG. 4 shows a detailed section of a further embodiment of a pen-type medication delivery device having a reusable or disposable cartridge holder unit.

The housing 1 comprises a proximal part 12 containing the delivery mechanism, which includes the piston rod 5. The disposable unit 111 comprises a distal part 11 of the housing 1 which serves as cartridge holder for a cartridge 121 contained in the distal part of the housing. The disposable unit further comprises locking means 113 formed as a clip and a cap 2 covering the part of the housing 1 which contains the cartridge 121. A fitting 114 of the disposable unit 111 is configured to be releasably connected with the proximal part 12 of the housing 1.

For delivering a dose the cap 2 is removed; then the piston rod 5 pushes the cartridge bung (not shown in FIG. 4) into the distal direction so that the drug is delivered. The cap 2 can be attached after delivery.

Delivery of the last dose results in engaging the locking means so that the cap 2 cannot be removed after attaching the cap. The lock-out principle is the same as described above.

For reusing the proximal part of the pen-type medication delivery device, the disposable unit 111 is removed, the piston rod 5 is reset and a new unit is attached.

It should be mentioned that the features of the embodiments can be combined.

REFERENCE NUMERALS 1 housing
2 cap
4 setting means
5 piston rod
6 bung
7 window
8 needle unit
9 needle
11 distal part of housing
12 proximal part of housing
16 first part of clip
17 second part of clip
18 aperture
21 proximal edge of cap
22 recess
31, 32, 33, 34 arrow
51 first part of piston rod
52 second part of piston rod
111 disposable unit
113 locking means
114 fitting of disposable unit
121 cartridge
171 distal edge of second part of clip
172 proximal edge of second part of clip
221 undercut

The invention claimed is:

1. A medication delivery device configured to contain a drug to be delivered, the medication delivery device comprising: a housing,
a cap configured to be: (i) removed from the housing and set aside during delivery of the drug and (ii) reattached to the housing after delivery of the drug, a moveable element, and
a locking portion configured to lock the cap and to function based on an amount of the drug that the medication delivery device contains when the cap is reattached, wherein the housing comprises an aperture,
wherein, in a first state in which the medication delivery device contains more than a predetermined amount of the drug, the cap is removable from the housing if the cap is reattached, and
wherein, in a second state in which the medication delivery device contains equal or less than the predetermined amount of the drug, the moveable element is configured to push the locking portion radially outward through the aperture in the housing such that the locking portion is configured to lock the cap if the cap is reattached over the locking portion.

2. The medication delivery device according to claim 1, wherein the medication delivery device is configured to deliver a multitude of doses of the drug and, when the last dose has been delivered, the cap is configured to lock if the cap is reattached.

3. The medication delivery device according to claim 2, wherein if the cap is reattached, the locking portion is configured to lock the cap when the moveable element is positioned in a given position, the given position being the position the moveable element reaches when a last dose is delivered, and
wherein the moveable element is configured to force the locking portion to protrude from the housing when the moveable element reaches the given position.

4. The medication delivery device according to claim 1, wherein the cap and the housing are configured to encapsulate the drug when the cap is locked.

5. The medication delivery device according to claim 1, wherein, if the cap is reattached, the locking portion is configured to lock the cap when the moveable element is positioned in a given position.

6. The medication delivery device according to claim 5, wherein the moveable element is moveable translationally and/or rotationally.

7. The medication delivery device according to claim 5, wherein the moveable element is designed as a piston rod.

8. The medication delivery device according to claim 5, wherein the cap comprises a mating section which is engageable with the locking portion, and wherein when the moveable element is located in the given position the locking portion is configured to protrude from the housing and is configured to be coupled with the mating section so that the cap is locked.

9. The medication delivery device according to claim 1, wherein the cap is configured to be permanently locked during the second state if the cap is reattached.

10. The medication delivery device according to claim 1, wherein the locking portion is integrally formed with the housing.

11. The medication delivery device according to claim 1, wherein the cap is permanently locked during the second state if the cap is reattached.

12. The medication delivery device according to claim 1, wherein the housing is configured to contain a replaceable cartridge and, when the cartridge is removed, the locked cap is unlocked.

13. The medication delivery device according to claim 1, wherein the housing comprises a disposable unit and, if the cap is locked, the disposable unit is removeable.

14. The medication delivery device according to claim 13, wherein the cap and the disposable unit are configured to encapsulate a cartridge.

15. The medication delivery device according to claim 1, wherein the medication delivery device is formed as pen-type medication delivery device.

\* \* \* \* \*